United States Patent [19]

Wallach

[11] 4,018,227
[45] Apr. 19, 1977

[54] CRYOSURGICAL INSTRUMENT

[75] Inventor: Ronald M. Wallach, Norwalk, Conn.

[73] Assignee: Cryomedics, Inc., Bridgeport, Conn.

[22] Filed: Oct. 9, 1975

[21] Appl. No.: 621,105

[52] U.S. Cl. ............................. 128/303.1; 62/293
[51] Int. Cl.[2] .................................... A61B 17/36
[58] Field of Search ............... 62/293; 128/303.1

[56] References Cited
UNITED STATES PATENTS

| | | | |
|---|---|---|---|
| 3,548,829 | 12/1970 | Reynolds et al. | 128/303.1 |
| 3,613,689 | 10/1971 | Crump et al. | 128/303.1 |
| 3,696,813 | 10/1972 | Wallach | 128/303.1 |
| 3,913,581 | 10/1975 | Ritson et al. | 128/303.1 |

Primary Examiner—Channing L. Pace
Attorney, Agent, or Firm—Barry Kramer

[57] ABSTRACT

A cryosurgical instrument having a purge cycle of indeterminate duration, separate and apart from its cooling and warming modes, which can be conducted with a refrigerant consisting of a low pressure unsaturated or saturated gas. During the purge cycle, the pressure of the refrigerant gas is regulated to a level below that which is required to effect a Joule-Thomson expansion of the gas upon its entrance into an expansion chamber adjacent the tip of the instrument while simultaneously exhausting the effluent to the atmosphere through an exhaust valve actuated by a footswitch.

13 Claims, 10 Drawing Figures

LEGEND

++++++++++ 760 P.S.I. (53.43 KG/CM²) TO 840 P.S.I. (59.06 KG/CM²)
────────── 480 P.S.I. (33.75 KG/CM²) TO 620 P.S.I. (43.59 KG/CM²)
── ── ── ── 100 P.S.I. (7.03 KG/CM²)
──·──·──·── EXPANDED GAS EXHAUSTING TO ATMOSPHERE

Fig. 1. STAND-BY TO PURGE MODE

Fig. 2. PURGE MODE

Fig. 3. STAND-BY TO FREEZE MODE OR DEFROST MODE

Fig. 4. FREEZE MODE

ALTERNATIVE STAND-BY TO FREEZE MODE OR DEFROST MODE

CRYOSURGICAL INSTRUMENT

BACKGROUND OF INVENTION

1. Field of the Invention

This invention relates to surgical apparatus, and more particularly, to an improved cryosurgical instrument.

2. Description of the Prior Art

Surgical techniques have been developed for necrosing, adhering and removing or coagulating defective or diseased body tissue by reducing the temperature of the tissue to relatively low values. Various cryosurgical instruments are known for aiding the medical practitioner in this form of treatment. Generally, these instruments include a probe tip which is initially placed in contact with the tissue to be treated and which is then cooled. The cooled probe tip is normally maintained in contact with the treated tissue for a short interval of time. The low temperature required for treatment must be attained rapidly after the probe tip contacts the tissue so that the tissue freezing is localized and the patient is not subjected to prolonged cold treatment. Additionally, it has been found that in certain treatment techniques, the body tissue undesirably adheres to a cooled treatment probe at these low temperatures and it is therefore necessary to provide means for rapidly warming the treatment probe in order to facilitate removal of the probe from the body tissue.

In a known form of cryosurgical instrument, a refrigerant gas under pressure is expanded into a chamber through a flow restriction thus producing a cooling effect commonly known as the Joule-Thomson effect. The probe tip, which is formed by an outer surface of the chamber, is thereby rapidly cooled. The instrument also incorporates means for effecting rapid warming of the probe tip in order to facilitate removal of the probe from the body tissue.

Various arrangements have been employed for cooling and for warming the probe tip. In one arrangement, the flow of a refrigerant gas to the expansion chamber is controlled by a valve located upstream from the chamber. Effluent gas from the chamber is exhausted to atmosphere. Cooling of the probe tip is accomplished by actuating the valve for enabling the flow of refrigerant gas to the expansion chamber and then to atmosphere. Warming of the probe tip is accomplished by interrupting the flow of gas to the expansion chamber and heating the probe tip by electrical means including a coil heater positioned in the probe tip.

In another cryosurgical instrument, probe tip cooling is provided by unseating a flow valve element located downstream of the expansion chamber and simultaneously forming a flow restriction at the chamber inlet by contacting an orifice seat with a moveable conduit. A refrigerant fluid then flows from a source, through the orifice and exhausts through the unseated downstream valve. Warming of the probe tip is accomplished by seating the downstream valve element and simultaneously separating the moveable conduit from the orifice seat thus permitting refrigerant fluid at ambient temperatures to flood the expansion chamber. Upon commencement of the cooling cycle, the instrument is purged of contaminants, such as dirt, ice particles and air bubbles. As the moveable conduit moves towards the orifice seat, refrigerant fluid flows from the source through the orifice momentarily before the conduit is seated on the orifice seat to form the flow restriction necessary to accomplish a Joule-Thomson expansion. This minute amount of unexpanded fluid is used to purge or flush the system of contaminant particles.

However, these arrangements as well as other various cryosurgical instrument arrangements are relatively complex and costly. At times they are relatively difficult for a medical practitioner to handle and do not provide him with the degree of manipulative facility necessary in a medical procedure where the practitioner must devote his close attention to the progress of the procedure. In addition, these known instruments do not provide a sufficient system for purging the instrument of contaminants, which may clog the flow restriction necessary for Joule-Thomson cooling, thereby rendering the instrument inoperative. This is particularly true when ice particles form in the flow restriction due to the rapid expansion of the refrigerant fluid.

In my prior U.S. Pat. No. 3,696,813, issued Oct. 10, 1972 to the same assignee as the present invention, I disclosed an improved cryogenic instrument utilizing the Joule-Thomson expansion principle for cooling the tip of the instrument which is placed in heat exchange relation with an expansion chamber. A quick acting two-way valve independent of and upstream from the expansion chamber is opened during cooling of the tip to exhaust the effluent refrigerating gas to the atmosphere, but upon closing causes interruption of the effluent gas flow to the atmosphere thereby trapping the refrigerant gas in the instrument at ambient temperature since the back pressure prevents further expansion of the incoming gas. This relatively large mass of high pressure gas at ambient temperature rapidly warms the tip thereby rapidly defrosting it.

SUMMARY OF THE INVENTION

The apparatus of this invention incorporates the discoveries and principles of construction used in my prior cryosurgical instrument disclosed in U.S. Pat. No. 3,696,813, with the additional improvement of a separate, safe purge cycle for flushing contaminants from the apparatus to prevent clogging of the instrument. As distinguished from the prior art, the purge of the instrument can be of indeterminate duration, separate and apart from its cooling and defrost, and can be conducted with a low pressure fluid.

These objectives are achieved by regulating the pressure of the refrigerant fluid to a level below that required to effect a Joule-Thomson expansion of said fluid prior to its entrance into the expansion chamber of the instrument and simultaneously exhausting the fluid to the atmosphere through an exhaust valve actuated by a footswitch. The low-pressure, ambient temperature gas will flow through the system as long as the footswitch is depressed to carry away with it any unwanted contaminants, such as dirt particles and air bubbles, and is of a temperature to melt or defrost any condensed ice particles formed adjacent the Joule-Thomson flow restriction. To accomplish cooling, the regulated gas is removed from the operational portion of the system circuit and a high-pressure refrigerant gas is supplied to the expansion chamber through a flow restriction or its Joule-Thomson equivalent, while the footswitch remains depressed to keep the exhaust valve open to exhaust the effluent to the atmosphere. Release of the footswitch closes the exhaust valve trapping the effluent gas in the system to cause defrost or warming of the instrument.

Further objects and advantages of the invention will become more apparent from the following description and claims, and from the accompanying drawings, wherein:

DETAILED DESCRIPTION OF THE PREFERRED EMBODIMENTS

Figure 1:
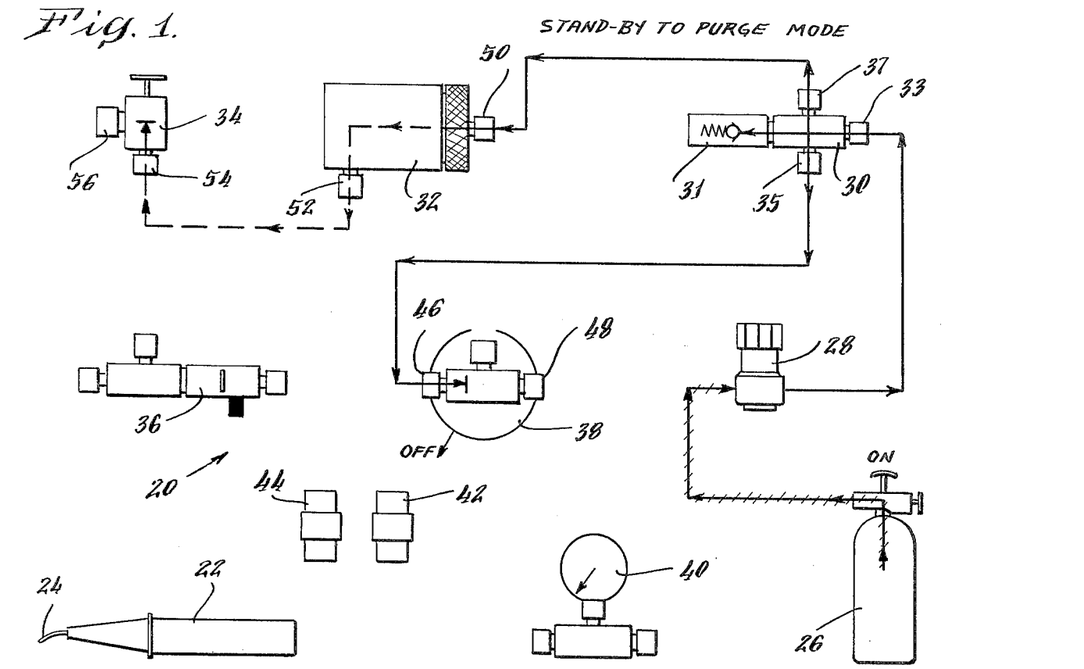
FIG. 1 is a diagrammatic view of the various components of the cryosurgical instrument of the present invention and illustrating the operation of the instrument in its stand-by condition to effect a purge cycle.

Referring now to the drawings in detail, wherein like numerals indicate like elements throughout the several views, the component parts of the cryosurgical instrument comprising the subject of the present invention are illustrated diagrammatically in FIG. 1.

The cryosurgical instrument 20 includes an ophthalmic probe 22. Probe 22 includes a tip 24 of high thermal conductivity material, such as silver, which when cooled, can be used for the extraction of cataractous lenses of the eye. In this operation, the lens is removed from the eye by means of the refrigerated probe tip 22 which is applied to the surface of the lens, to adhere it to the tip. The ice ball which is thereby formed within the fluid and tissue of the lens permits the force exerted by the surgeon's hand to be spread over a wide area, permitting adhesion and withdrawal of the lens by the tip with greatly reduced chances of rupture. Other tip configurations can be employed without departing from the scope of the invention, such as a tip for "welding" or coagulating a detached retina, or even a probe attached to a pistol grip device as illustrated in U.S. Pat. No. 3,696,813, which is used for tissue necrosis.

In any event, each probe includes an expansion chamber adjacent the probe tip and means for conveying a gaseous or two-phase liquid-gas or saturated gas refrigerant from a source to the expansion chamber. The means includes a stationary body defining a flow restriction through which the gas is introduced into the chamber to effect a Joule-Thomson expansion of the gas to cool the chamber. The flow restriction may take many forms, such as an orifice, a porous plug, a throttle valve, or a capillary tube, so long as there is a large drop in pressure as the gas passes through the flow restriction into the expansion chamber to produce a drop in temperature of the gas under isenthalpic conditions.

If a two-phase refrigerant is supplied to the expansion chamber, e.g., a saturated gas having a liquid and gaseous phase which are intermixed, the refrigerant will flow into said expansion chamber and expand the gaseous phase into the chamber providing a Joule-Thomson refrigeration effect and additional cooling of the chamber is accomplished by the evaporation of the liquid phase therein. A saturated gas exhibits a high thermal conductivity relative to unsaturated gas and is therefore preferred as an efficient heat transfer medium for removing heat from the chamber. Exemplary gases for use in the instrument comprise carbon dioxide ($CO_2$) and nitrous oxide ($N_2O$).

The other components of the instrument 20 include a refrigerant gas supply 26, an adjustable pressure regulator 28, a cross 30 with a pressure relief valve extension 31, a fixed pressure regulator 32, a footswitch 34, a valve and actuator 36, a manually operable valve 38, a pressure gauge 40, a probe inlet hose connector fitting 42 and a probe outlet hose connector fitting 44. Hoses are not shown in the diagrammatic views, but it will be understood that appropriate hose conduits are provided between the various components of instrument 20 to conduct the flow of refrigerant gas as depicted in FIGS. 1 to 5.

In accordance with the principles of this invention, the operation of the instrument 20 is initiated by turning on the gas supply cylinder 26. Gas from the cylinder 26, which is typically under 760 to 840 p.s.i. at 70° F. depending on the refrigerant used, has its cylinder pressure regulated by pressure regulator 28 (as shown in FIG. 1) to 480 – 620 p.s.i. for safety reasons. A typical regulator 28 which can be used in the system is manufactured by the Veriflo Corporation of Richmond, California, Series No. IR403.

The regulated gas flows to the inlet 33 of cross 30 and pressure relief valve extension 31 will open and relieve the system if the system pressure at inlet 33 is above 675 p.s.i. If not, the regulated gas flows through outlet 35 of cross 30 into an inlet 46 of valve 38 and temporarily stops as the outlet 48 is not in communication with inlet 46 when the manual control is placed in the OFF position, as illustrated in FIG. 1. Simultaneously, another leg of the regulated gas flows through a second outlet 37 of cross 30 to the inlet 50 of fixed pressure regulator 32, is regulated by having its pressure reduced to 100 p.s.i., and travels from outlet 52 of regulator 32 to inlet 54 of the footswitch 34, which is closed in the position illustrated in FIG. 1 to prevent communication between the inlet 54 and its outlet 56 so that the gas also temporarily stops at this point. As no gas flows through pressure gauge 40, it reads 0 p.s.i. The instrument 20 is now in a stand-by condition to be purged and this state is fully illustrated in FIG. 1.

Pressure regulators 28 and 32, as well as cross 30 and valve 38, pressure gauge 40, valve and actuator 36, and footswitch 34 are standard hardware items and per se, form no part of the present invention. Pressure regulator 32 is manufactured by C. A. Norgren Co. of Littleton, Colorado, Model No. R37-100-N100A, while valve 30 is sold by the Lindco Co. of Worester, Massachusetts, under the trademark CIRCLE SEAL, valve 38 is sold under the trademark WHITEY by the Norwalk Valve Co. of Shelton, Connecticut, valve and actuator 36 is sold under the trademark CLIPPARD by Knox, Inc. of Bridgeport, Connecticut, pressure gauge 40 is manufactured by U.S. Gauge Co. of Somersville, Pennsylvania and sold under the trademark AMETEK, and footswitch 34 is manufactured by Linemaster Co. of Woodstock, Connecticut.

Figures 7, 9:
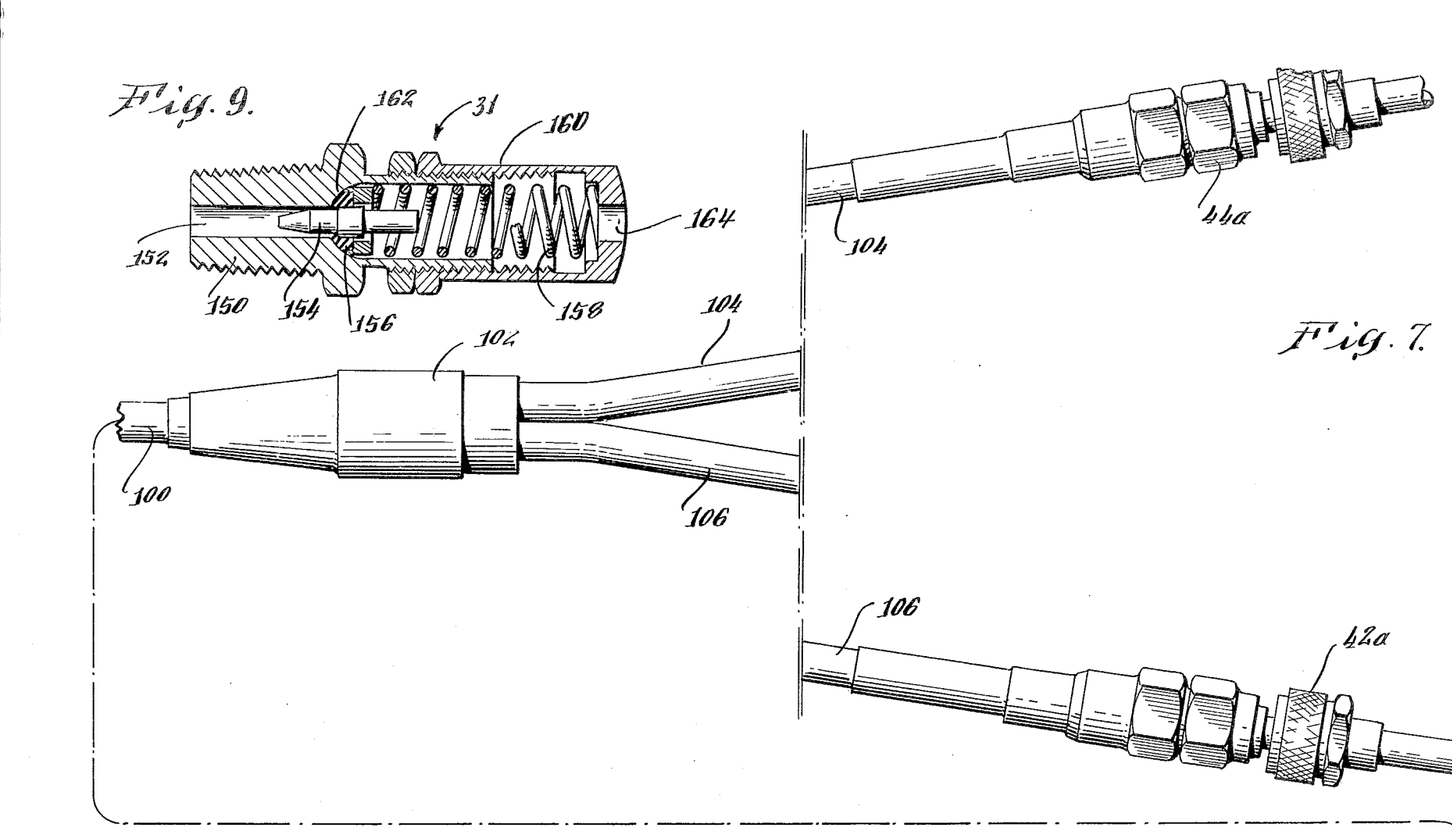
FIG. 7 is an expanded view of a portion of the instrument diagrammatically illustrated in FIG. 1, including a longitudinal cross-sectional view of a typical opthalmic probe component.
FIG. 9 is a longitudinal cross-sectional view of the pressure relief valve component of the instrument diagrammatically illustrated in FIG. 1.

Pressure relief valve extension 31 is shown in detail in FIG. 9. Valve extension 31 included a pipe nipple 150 which is threaded onto the housing of cross 30 so that communication is established between inlet 33 of cross 30 and normally closed inlet orifice 152 in pipe nipple 150. Inlet orifice 152 is normally closed by a valve element 154 fixed to a seal 156 which is urged by a coil spring 158 in valve housing 160 into seated engagement with valve seat 162 at the distal end of inlet orifice 152. Coil spring 158 is calibrated to hold seal 156 against valve seat 162, and consequently valve element 154 in blocking relation closing orifice 152, until the pressure exerted against it exceeds 675 p.s.i. Should this occur, gas will flow past seal 156 into valve housing 160 and be expelled to the atmosphere through outlet port 164 in the valve housing.

Figure 2:
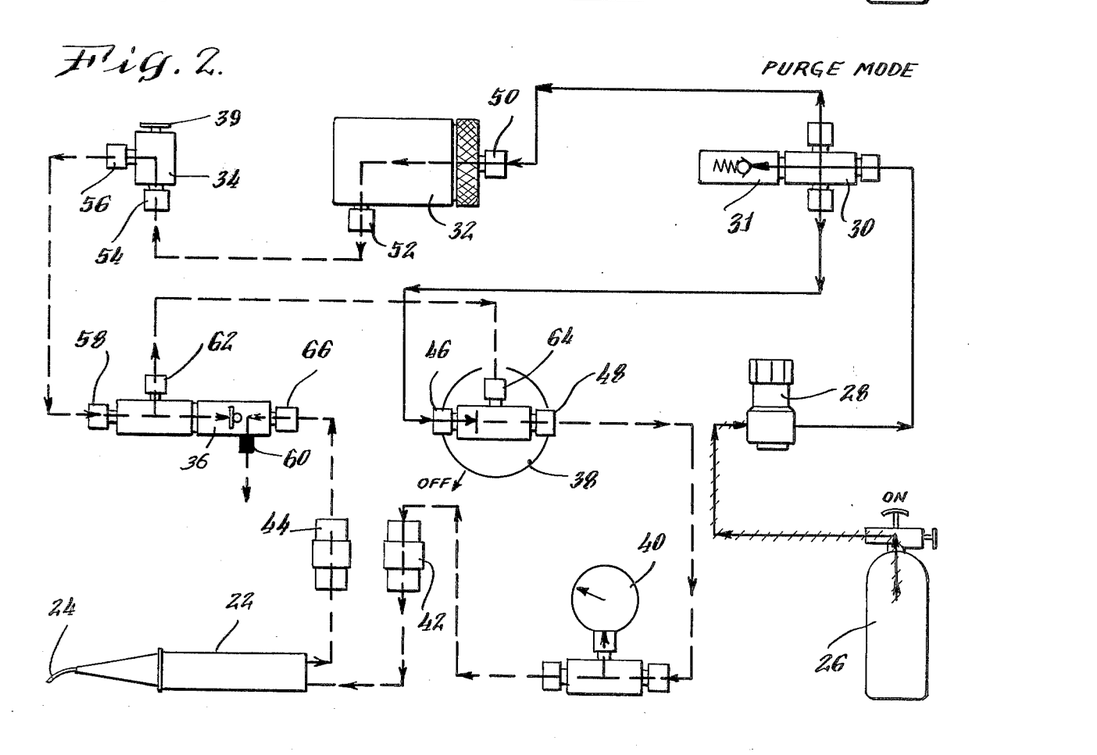
FIG. 2 is a view similar to FIG. 1 illustrating the operation of the instrument in its purge mode.

In order to purge the instrument of contaminants such as residual moisture or dirt, the 100 p.s.i. refrigerant gas is circulated through probe 22, as shown in FIG. 2 by stepping on and depressing stem 39 of footswitch 34. This establishes communication between inlet 54 and outlet 56 of footswitch 34 and 100 p.s.i. regulated gas flows from the outlet 56 to the inlet 58 of valve and actuator 36. The presence of gas within valve and actuator 36 causes an exhaust port 60 to open, while the regulated gas exits through outlet 62 in valve and actuator 36 and is fed through a second inlet port 64 to valve 38. When manual valve 38 is in its OFF position, inlet 64 is in communication with outlet 48 and the regulated gas is then free to pass through pressure gauge 40, coupling 42, probe 22, coupling 44, a second inlet 66 in valve and actuator 36 and exhaust to the atmosphere through an exhaust port 60. The circulation of the regulated gas through probe 22 provides a flushing action which will remove any contaminants from the probe and its attendant conduits. Since the gas is at 100 p.s.i., there is an insufficient pressure differential created across the flow restriction in probe 22 for the gas to provide sufficient cooling of tip 24 due to a Joule-Thomson expansion. The purge mode is fully illustrated in FIG. 2 and can be of any duration as long as valve 38 is in the OFF position, and footswitch 34 is depressed. During this cycle, gauge 40 will read 100 p.s.i. Release of footswitch stem 39 returns the instrument to its stand-by to purge mode illustrated in FIG. 1.

Figure 3:
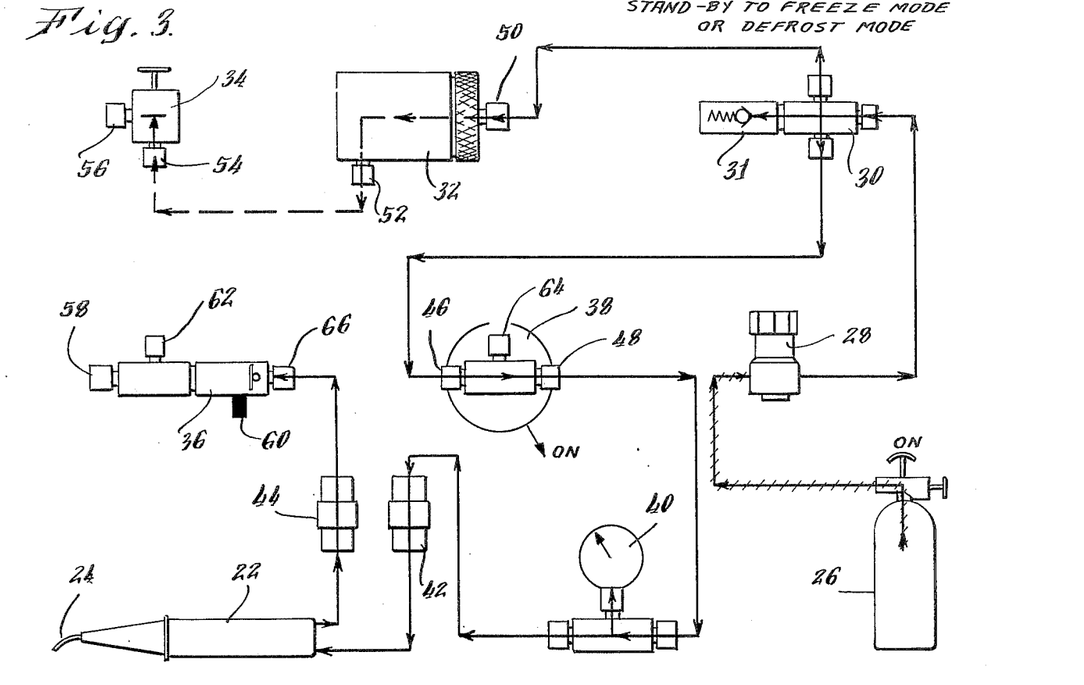
FIG. 3 is a view similar to FIG. 1 illustrating the operation of the instrument in its stand-by condition to effect a cooling cycle or in its warming or defrost mode.

In order to prepare the instrument 20 to effect cooling of tip 24 of probe 22, it is only necessary to manually place valve 38 in its ON position, as illustrated in FIG. 3. This will establish communication between inlet 46 and outlet 48 to permit the high pressure gas at 480 – 620 p.s.i. to flow through valve 38, pressure gauge 40, coupling 42, probe 22, coupling 44 and into inlet 66 of valve and actuator 36. Since exhaust port 60 is closed because footswitch stem 39 has not been depressed, gas pressure will build up upstream from the expansion chamber in probe 22 so that any Joule-Thomson expansion through the flow restriction in probe 22 is neutralized, precluding a temperature drop of the gas within the expansion chamber so that it remains at substantially ambient temperature. However, pressure gauge 40 will read 480 – 620 p.s.i., and this condition of the instrument is fully illustrated in FIG. 3.

Figure 4:
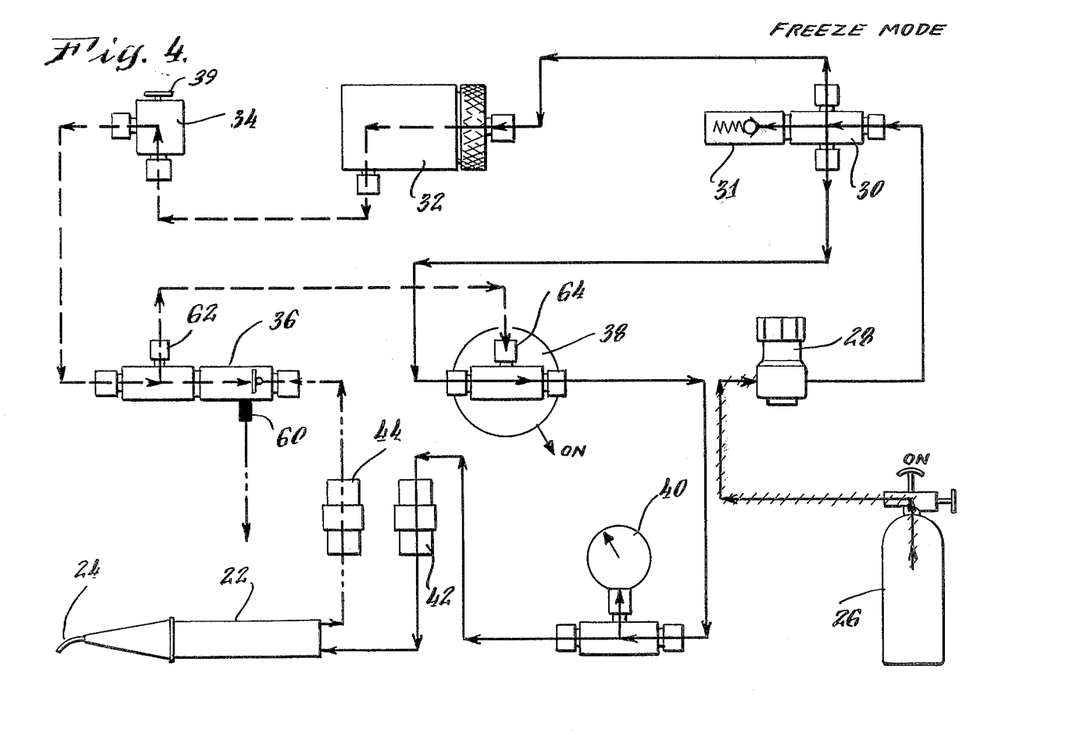
FIG. 4 is a view similar to FIG. 1 illustrating the operation of the instrument in its cooling mode.

In order to effect cooling of tip 24 of probe 22, the surgeon need only depress the footswitch stem 39, as illustrated in FIG. 4. This will allow the low pressure 100 p.s.i. regulated gas to flow through the footswitch to the actuator and valve 36, opening exhaust port 60. The low pressure gas flows from outlet 62 of actuator and valve 36 to the inlet 64 of valve 38. Since valve 38 is on ON, however, the flow of the low pressure gas stops at this point in the system. But, the high pressure gas will continue to flow through valve 38 through probe 22, and can now exhaust to the atmosphere through exhaust port 60. This will relieve the back pressure downstream from the flow restriction in probe 22 and permit a Joule-Thomson expansion to progress. The cooled gas in the expansion chamber adjacent tip 24 will cool it by heat-exchange therewith. Freezing at tip 24 will continue as long as footswitch 34 is depressed and pressure gauge 40 will continue to read 480 – 620 p.s.i.

In order to warm the tip 24 and cause it to defrost, it is only necessary to release footswitch stem 39 to return the instrument to its mode illustrated in FIG. 3, wherein the supply of low pressure gas to the actuator and valve 36 is cut-off so exhaust port 60 is closed. The accumulated back pressure upstream from the expansion chamber in the probe 22 will preclude further Joule-Thomson expansion and the instrument will be filled with high pressure gas at ambient temperature. Heat transfer between this gas and the tip 24 of probe 22 will rapidly defrost the tip.

Figure 5:
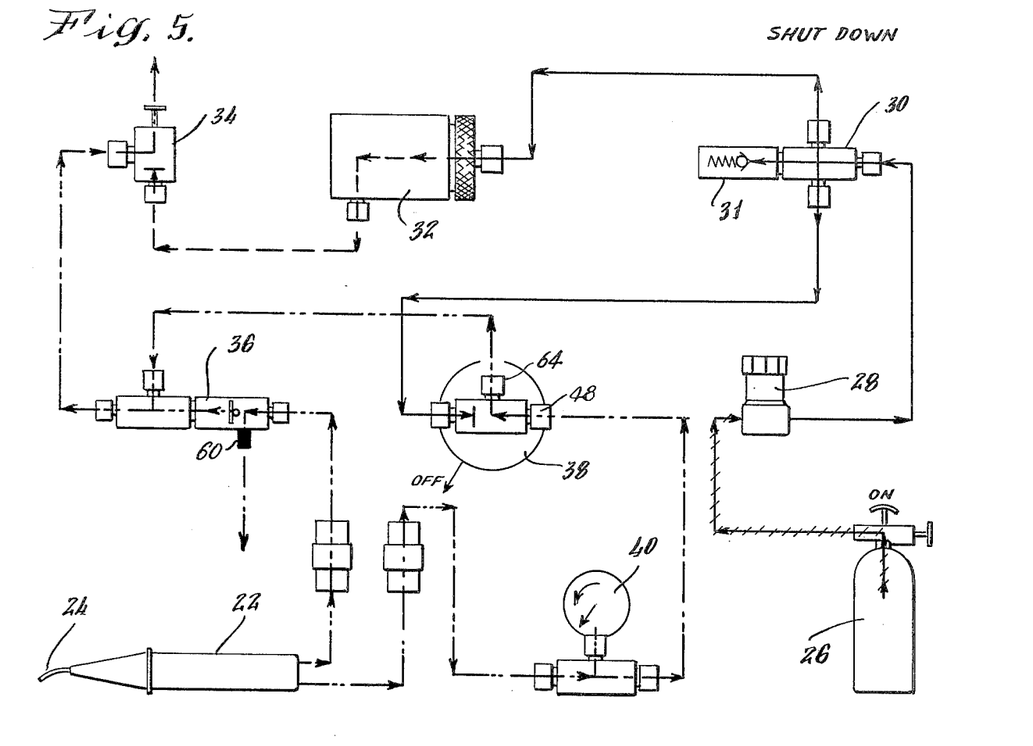
FIG. 5 is a view similar to FIG. 1 illustrating the manner of shutting down the instrument.
Figure 6:
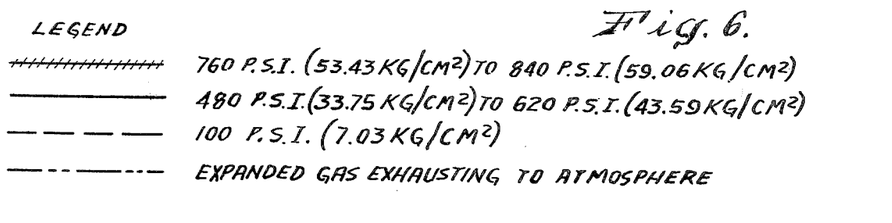
FIG. 6 is a legend defining the various flow pressures of the refrigerant flowing through the instrument in FIGS. 1 to 5.

Shut down of the instrument is illustrated in FIG. 5. With the operation finished, and footswitch 34 released, valve 38 is returned to the OFF position, which positions outlet 48 in communication with inlet 64 in valve 38. In this condition, instrument 20 has been returned to the stand-by to freeze mode illustrated in FIG. 3. This releases the gas pressure in the probe and most of the system. Probe 22 can now be disconnected from the supply 26 and any residual expanded gas within the system can be exhausted to the atmosphere as shown in FIG. 5 by the dot-dash lines. Exhaust pot 60 in actuator and valve 36 is opened by the residual pressure in probe 22 to exhaust the residual upstream gas to the atmosphere, while the downstream residual gas reverses its flow path and is exhausted through footswitch 34 via valve 38 and valve 36.

Details of a typical probe construction 22a used in cryosurgical instrument 20 and particularly useful for removal of cataractous eye lenses, are shown in FIG. 7. Probe 22a includes an elongated tubular body 70 forming a convenient gripping handle for the surgeon. Body 70 is rigidified adjacent its forward end by a tubular nose portion 72 of expanded thickness. An exhaust tube assembly 74 is positioned and fixed within the tubular nose portion 72 and includes an exhaust tube 76 coaxial with and concentric to a flow restriction comprising a capillary tube 78. The forward end of the exhaust tube terminates in a tip 24a of high thermal conductive material, such as silver. Capillary tube 78 terminates at its forward end in spaced relation to tip 24a to form a Joule-Thomson expansion chamber 80.

At its distal end, exhaust tube 76 has a tubular extension 82, which is fixed to a standard tube fitting 84, which connects exhaust tube extension 82 to an exhaust conduit 86. Communication between exhaust tube extension 82 and exhaust conduit 86 is provided via an opening 88 in the central portion of tube fitting 84.

At its distal end, capillary tube 78 is fixed to a tube 90 which in turn is locked in place within a second, standard tube fitting 92, which also holds the forward end of a refrigerant gas inlet conduit 94. Communication between capillary tube 78 and inlet conduit 94 is provided via an opening 96 in the central portion of tube fitting 92. A retaining collar 98 locks a protective sheath 100 for the inlet conduit 94 and exhaust conduit 86 to probe 22a.

The inlet conduit 94 and exhaust conduit 86 project beyond the end of protective sheath 100 and are split apart in a shrink tube or connector 102 and the exhaust and inlet conduits are enclosed in a sheath 104 and 106, respectively, which in turn are attached to connector fittings 44a and 42a, respectively, whose function has been disclosed in connection with FIGS. 1 to 5.

In operation, high or low pressure gas, depending upon which mode of operation the instrument is in, is supplied to the probe 22a through inlet conduit 94. Direction of flow of the gas is indicated by the arrows in FIG. 7. The gas passes through opening 96 in tube fitting 92, enters tube 90 and capillary tube 78 which passes through tube fitting 84. The gas is discharged through the end of the capillary tube 78 into the expansion chamber 80, wherein if exhaust port 60 of valve 36 is open and the gas is at a high pressure of between 480 and 620 p.s.i., it will undergo a Joule-Thomson expansion in chamber 80, cooling tip 24a. The effluent gas passes through exhaust tube 76 in concentric relation to capillary tube 78, through exhaust tube extension 82, opening 88 in tube fitting 84 into exhaust conduit 86 from which it is vented to the atmosphere. Upon closing of exhaust port 60, the gas pressure in the exhaust conduit 86 and the exhaust tube 76 will build up, precluding a substantial drop in pressure of the gas entering the expansion chamber 80 through capillary tube 78. As the gas entering chamber 80 is at ambient temperature, it will defrost the tip 24a through heat exchange with the tip. With low pressure, i.e., 100 p.s.i. gas flowing through capillary tube 78, no Joule-Thomson expansion occurs in chamber 80, and the effluent passes to the atmosphere as described above. However, such gas will purge the component parts of probe 22a, as well as the inlet and exhaust conduits of any foreign matter which may tend to clog expansion chamber 80. Any residual ice particles in capillary tube 78 or the exhaust tube 76 will also melt.

By pre-cooling the saturated refrigerant gas which is flowing through the capillary tube 78, there is provided both a vapor and a liquid phase refrigerant. The vapor phase expands in accordance with the Joule-Thomson effect and provides a refrigerating effect thereby cooling the tip 24a. In cooperation with this cooling effect, the liquid phase which can be provided by pre-cooling is sprayed into the expansion chamber 80 and absorbs a quantity of heat over a period of time equivalent to its latent heat of vaporization. It has been found that the combined cooling established by this combination of Joule-Thomson effect and the latent heat of vaporization rapidly lowers the temperature of the probe 22a and provides very rapid cooling of the tip 24a.

It will also be understood that probe 22a can operate with a saturated gas having both an intermixed liquid and gaseous phase. Both phases will enter expansion chamber 80 through capillary tube 78. The liquid phase refrigerant remains within the expansion chamber for a short interval of time during which time it absorbs latent heat of vaporixation. Thus, a double cooling action is provided which is highly desirable.

The construction of probe 22a does provide for this pre-cooling effect during the cooling mode, since the cold effluent gas is passed into heat exchange relation with the capillary tube 78 by virtue of the exhaust tube 76 surrounding the capillary tube in concentric relation.

Figure 8:
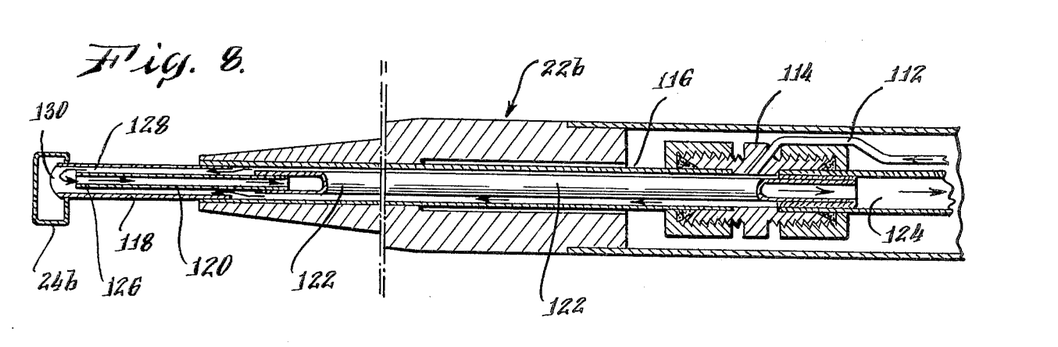
FIG. 8 is a view similar to FIG. 7, but illustrating a modified form of probe.

However, in some types of ophthalmic surgical procedures, the pre-cooling effect accomplished by probe construction 22a can be detrimental, particularly where the forward portion 110 of the exhaust tube 76 attached to tip 24a must contact a portion of the eye as well as tip 24a. Because of the cold effluent gas passing on the outside of capillary tube 78, the forward portion 110 of exhaust tube 76 will be cooled as well as tip 24a and this may be detrimental to the surgical technique if portion 110 freezes adjacent tissue when the probe is passed into the eye. In order to prevent such an occurrence, probe 22b as illustrated in FIG. 8 may be used with cryosurgical instrument 20.

Probe 22b is similar in construction to probe 22a except for the inlet and exhaust tube assemblies. In probe 22b inlet conduit 112 passes through a tube fitting 114 and delivers the gaseous refrigerant to an inlet tube 116, having one end held fixed by tube fitting 114. Inlet tube 116 includes a forwardly projecting extension 118 terminating in a tip 24b, particularly useful for retinal coagulation. An exhaust tube 120 is positioned within and concentric to inlet tube extension 118. Exhaust tube 120 has an extension 122 which is coupled by tube fitting 114 to an exhaust conduit 124. The extreme forward end 126 of exhaust tube 120 is enlarged in diameter so as to form a Joule-Thomson flow restriction by providing an annular space or orifice 128 between forward end 126 of exhaust tube 120 and inlet tube 116. Orifice 128 terminates in an expansion chamber 130 in heat exchange relation with tip 24b.

In probe construction 22b, incoming high pressure ambient refrigerant gas will traverse the annular space between inlet tube 118 and exhaust tube 120 and expand through the annular space at flow restriction 128 into expansion chamber 130 to cool tip 24b. The effluent will leave through the interior exhaust tube 118 to the atmosphere. Because of this arrangement, the colder effluent gas is not placed in heat exchange relation with inlet tube 118, but rather the incoming ambient gas serves to insulate the tube surface to preclude cooling thereof. In all other respects, operation operation of probe 22b is identical to probe 22a.

It has also been found that the capillary tube 78 in probe 22a or one of the conduits in probe 22b may become plugged with ice crystals caused by condensed refrigerant vapor, if either probe is left in its stand-by to freeze or defrost mode for an extended period of time. This time has been found to be in excess of 3 to 10 minutes, depending on the type of the probe.

Figure 10:
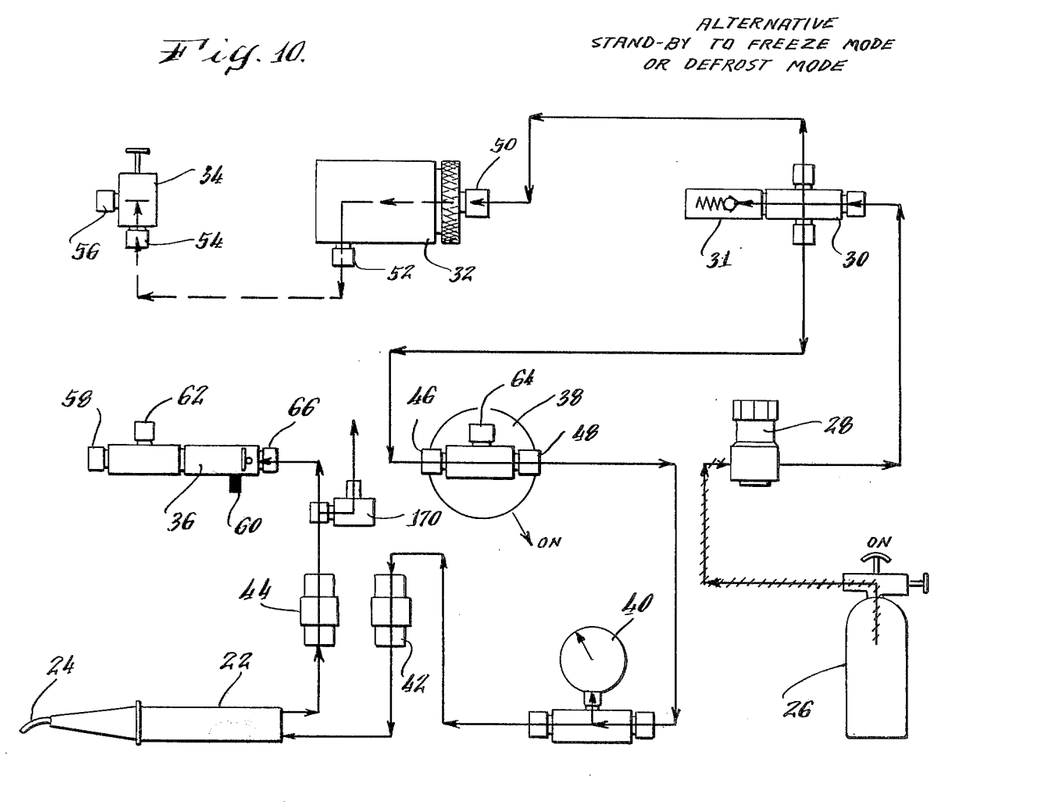
FIG. 10 is a view similar to FIG. 3, but illustrating an alternative stand-by condition to effect a cooling cycle.

In order to avoid this problem an alternative stand-by to freeze or defrost cycle as illustrated in FIG. 10 can be utilized in the operation of the instrument. In this embodiment of the invention, a bleed valve 170 is placed between the outlet of the probe 22 and the inlet 66 to exhaust port 60. Bleed valve 170 enables a continuous flow of high pressure gas to be bled from the probe 22 when exhaust port 60 is closed without impairing the freeze or defrost abilities of probe 22. The small amount of flow through valve 170, which can be of the standard needle type, can be on the order of 1.3 to 1.4 scfh at an input pressure of between 480 to 620 p.s.i. The bleeding of the high pressure gas precludes refrigerant vapor from being in contact with the components of the probe for too long a protracted period of time so as to prevent the vapor from condensing on the components to form ice crystals which can plug the components.

However, during the freeze or purge cycles of the instrument, the gas will take the path of least resistance, which is through exhaust port 60, thereby not effecting the freeze, defrost or purge modes of the instrument illustrated in FIGS. 1 to 5, inclusive.

What is claimed is:

1. A cryosurgical instrument comprising:
   means defining an expansion chamber, said means including
   a body formed of a high thermal conductivity material and having a surface thereof shaped for contacting body tissue and providing heat transfer with the tissue,
   refrigerant supply means for conveying a gaseous refrigerant under pressure from a source to said expansion chamber, said means including
   flow restriction means adjacent said chamber for providing an appropriate pressure differential as said pressurized gas passes therethrough to cause a Joule-Thomson expansion of said gas to cool said chamber,
   selectively operable pressure regulation means for reducing the pressure of said gaseous refrigerant below that required to effect said Joule-Thomson expansion of said gas prior to its entrance into said expansion chamber, and
   selectively operable exhaust means for conveying an effluent gas from said chamber to the atmosphere, whereby with said pressure regulation means in its inoperative mode and said exhaust means in its operative mode, said gas can expand into said chamber and exhaust to the atmosphere to effect rapid cooling of said chamber; with said pressure regulation means in its inoperative mode and said exhaust means in its inoperative mode,
   said gas flow to the atmosphere can be interrupted thereby effecting rapid warming of said chamber; and with said pressure regulation means in its operative mode and said exhaust means in its operative mode said gas will not undergo a Joule-Thomson expansion but will flow through and purge said refrigerant supply means, chamber, and exhaust means of contaminants.

2. A cryosurgical instrument in accordance with claim 1 wherein said exhaust means includes
   an exhaust valve, and
   an exhaust flow channel for said effluent gas in communication with said expansion chamber and said exhaust valve.

3. A cryosurgical instrument in accordance with claim 2 including means for selectively actuating said exhaust valve to open it to the atmosphere, said means including a foot-actuated gas switch.

4. A cryosurgical instrument in accordance with claim 1 wherein said flow restriction means includes a capillary tube.

5. A cryosurgical instrument in accordance with claim 1 wherein said refrigerant supply means includes valve means for providing a flow path for said pressurized gas to the atmosphere when the pressure within said instrument exceeds a predetermined safe pressure.

6. A cryosurgical instrument in accordance with claim 2 wherein said refrigerant supply means includes an elongated supply conduit means, said flow restriction means is positioned near a distal end of said supply conduit means, means are provided for supplying a gaseous refrigerant to an inlet end of said supply conduit means, said exhaust flow channel is formed by exhaust conduit means which is positioned with relation to said supply conduit means for forming an annular space therebetween, and said exhaust valve is coupled in a flow path between said exhaust conduit means and the atmosphere.

7. A cryosurgical instrument in accordance with claim 6 wherein at least a portion of said supply and exhaust conduit means are concentrically oriented, said supply conduit means being positioned inside said exhaust conduit means.

8. A cryosurgical instrument in accordance with claim 7 wherein said portion of said supply conduit means concentrically oriented with respect to said exhaust conduit means is a capillary tube.

9. A cryosurgical instrument in accordance with claim 6 wherein at least a portion of said supply and exhaust conduit means are concentrically oriented, said exhaust conduit means being positioned inside said supply conduit means.

10. A cryosurgical instrument in accordance with claim 1 wherein said flow restriction means is a stationary body.

11. In a method for cooling and warming an applicator head of a cryosurgical instrument in contact with body tissue which comprises the steps of:
    1. conveying a gaseous refrigerant at substantially ambient temperature and relatively high pressure toward a stationary flow restriction means communicating with an expansion chamber in the head of the instrument;
    2. introducing the refrigerant through said stationary flow restriction means into the expansion chamber, said chamber being in contact with the applicator head of said instrument, and effecting a Joule-Thomson expansion of said gaseous refrigerant thereby cooling said expansion chamber; and
    3. conveying an effluent gas from said expansion chamber to the atmosphere during cooling of said chamber and then cutting off the flow of said effluent gas trapping a sufficient body of gaseous refrigerant at substantially ambient temperature within said instrument to effect rapid warming of said chamber, the improvement comprising:
    4. purging said instrument of contaminants by reducing the pressure of said gaseous refrigerant prior to its entrance into said expansion chamber below that necessary to effect said Joule-Thomson expansion of said gas while,
    5. conveying an effluent gas from said expansion chamber to the atmosphere.

12. A cryosurgical instrument in accordance with claim 1 including
    bleed valve means between said selectively operable exhaust means and said expansion chamber, said bleed valve means enabling a continuous bleed of effluent gas from said expansion chamber to atmosphere.

13. A cryosurgical instrument comprising:
    means defining an expansion chamber, said means including a body formed of a high thermal conductivity material and having a surface thereof shaped for contacting body tissue and providing heat transfer with the tissue, refrigerant supply means for conveying a gaseous refrigerant under pressure from a source to said expansion chamber, said means including flow restriction means adjacent said chamber for providing an appropriate pressure defferential as said pressurized gas passes therethrough to cause a Joule-Thomson expansion of said gas to cool said chamber, selectively operable exhaust means for conveying an effluent gas from said chamber to the atmosphere, and bleed valve means between said selectively operable exhaust means and expansion chamber, said bleed valve means enabling a continuous bleed of effluent gas from said expansion chamber to atmosphere.

* * * * *